United States Patent [19]

DeVries et al.

[11] Patent Number: 4,603,145

[45] Date of Patent: Jul. 29, 1986

[54] ANTIATHEROSCLEROTIC DIPHENYL ALKANAMIDES

[75] Inventors: Vern G. DeVries, Ridgewood, N.J.; Robert G. Shepherd, Selbyville, Del.; Janis Upeslacis, Pomona, N.Y.

[73] Assignee: American Cyanamid Company, Stamford, Conn.

[21] Appl. No.: 492,096

[22] Filed: May 6, 1983

[51] Int. Cl.[4] .................. A61K 31/22; A61K 31/165; C07C 103/84; C07C 103/78

[52] U.S. Cl. .................... 514/539; 514/563; 514/617; 514/622; 514/824; 560/36; 562/441; 564/174; 564/181

[58] Field of Search ............... 564/171, 174, 155, 158, 564/181; 424/324; 560/36; 71/118; 562/441; 514/539, 563, 622, 617, 824

[56] References Cited

U.S. PATENT DOCUMENTS

| | | | |
|---|---|---|---|
| 3,296,305 | 1/1967 | Doering et al. | 564/181 |
| 3,346,634 | 10/1967 | Christensen et al. | 564/181 |
| 3,361,790 | 1/1968 | Allen et al. | 562/441 X |
| 3,736,347 | 5/1973 | Billett et al. | 564/171 |
| 3,895,057 | 7/1975 | Kaneko et al. | 564/181 |
| 4,392,884 | 7/1983 | Pallos et al. | 71/118 X |

FOREIGN PATENT DOCUMENTS 217009 7/1984 Czechoslovakia .
3018114 11/1981 Fed. Rep. of Germany .

OTHER PUBLICATIONS

Miyamoto et al, *Tetrahedron Letters*, No. 25, pp. 2155–2156, 1978.
Work et al, CA 60:10590c.
Troxler, CA 71:13032c.
Popandova, CA 80:95438n.
*Chemical Abstracts:* Vol. 36, 1604(9); vol. 50, 4059(c); vol. 51, 15465 (a).

*Primary Examiner*—Charles F. Warren
*Assistant Examiner*—C. S. Greason
*Attorney, Agent, or Firm*—Edward A. Conroy, Jr.

[57] ABSTRACT

This disclosure describes novel diaryl-alkanamides. These compounds are useful as pharmaceutical agents for ameliorating atherosclerosis by inhibiting the formation and development of atherosclerotic lesions in the arterial wall of mammals.

7 Claims, No Drawings

ANTIATHEROSCLEROTIC DIPHENYL ALKANAMIDES

BACKGROUND OF THE INVENTION

This invention relates to new organic compounds useful as pharmaceutical agents. The novel compounds of the present invention are antiatherosclerotic agents capable of ameliorating atherosclerosis by counteracting the formation or development of atheromatous lesions in the arterial wall of mammals. The invention also relates to the chemical synthesis of the novel compounds disclosed herein. In addition, the invention pertains to novel pharmaceutical compositions for the utilization of these compounds in the treatment of disease in mammals. Further, the invention contemplates methods for treating atherosclerosis in a manner designed to prevent, arrest, or reverse the course of the disease.

Atherosclerosis is a form of arteriosclerosis characterized by lipid accumulation in and thickening of the arterial walls of both medium- and large-sized arteries. Arterial walls are thereby weakened, and the elasticity and effective internal size of the artery is decreased. Atherosclerosis is the most common cause of coronary artery disease and is of great medical importance since the occlusion of medium- and large-sized arteries diminishes the supply of blood to vital organs such as the heart muscles and the brain. The sequelae to atherosclerosis include ischemic heart disease, heart failure, life-threatening arrythmias, senility, and stroke.

The fact that cholesterol is a major component of atherosclerotic lesions or plagues has been known for more than 100 years. Various researchers have studied the role of cholesterol in lesion formation and development and also, more importantly, whether lesion formation can be prevented or lesion development arrested or reversed. Atheromatous lesions have now been shown [Adams, et al., Atherosclerosis, 13, 429 (1974)] to contain a greater quantity of esterified as opposed to unesterified cholesterol than the surrounding undiseased arterial wall. The intracellular esterification of cholesterol with fatty acids is catalyzed by the enzyme "Fatty acyl CoA: cholesterol acyl transferase" or ACAT, and the accumulation and storage of cholesterol esters in the arterial wall is associated with increased levels of this enzyme [Hashimoto and Dayton, Atherosclerosis, 28, 447 (1977)]. In addition, cholesterol esters are removed from cells at a slower rate than unesterified cholesterol [Bondjers and Bjorkerud, Atherosclerosis, 15, 273 (1972) and 22, 379 (1975)]. Thus, inhibition of the ACAT enzyme would diminish the rate of cholesterol esterification, decrease the accumulation and storage of cholesterol esters in the arterial wall, and prevent or inhibit the formation and development of atheromatous lesions. The compounds of the present invention are very potent inhibitors of the ACAT enzyme. Thus, these compounds are useful for controlling and normalizing the cholesterol ester content of mammalian arterial walls. In contrast to the serum hypocholesterolemic agents which are well known in the art to merely lower cholesterol in the blood stream, the compounds of this invention decrease the accumulation and storage of cholesterol in the arterial walls of mammals. Further, the compounds of this invention inhibit the formation or development of atherosclerotic lesions in mammals. The exact mechanism by which these compounds exhibit this antiatherosclerotic activity is not known and the invention should not be construed as limited to any particular mechanism of antiatherosclerotic action.

SUMMARY OF THE INVENTION

This invention relates to new organic compounds and more particularly is concerned with diaryl alkanamides which may be represented by the following structural formula:

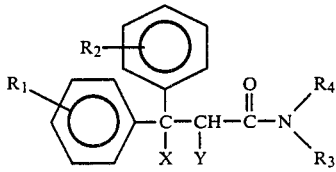

wherein $R_1$ and $R_2$ are independently selected from the group consisting of hydrogen, $C_1$–$C_4$ alkyl, $C_1$–$C_4$ alkoxy, and halo; X and Y are each hydrogen or, when taken together, represent a carbon-carbon bond; $R_3$ and $R_4$ are independently selected from the group consisting of hydrogen, $C_1$–$C_{10}$ alkyl, benzyl, phenethyl, 3,4-dimethoxyphenethyl, adamantyl, carboxymethyl, and ($C_1$–$C_4$ carboalkoxy)methyl with the proviso that $R_3$ and $R_4$ cannot both be hydrogen; and the pharmaceutically-acceptable salts thereof.

Preferred embodiments of the invention involve compounds wherein $R_1$ and $R_2$ are $C_1$–$C_4$ alkyl, $C_1$–$C_4$ alkoxy, or halo. More preferred embodiments involve compounds wherein $R_1$ and $R_2$ are methyl, methoxy, or chloro. The most preferred embodiments involve compounds wherein $R_1$ and $R_2$ are methyl, methoxy, or chloro; and $R_3$ and $R_4$ are $C_1$–$C_{10}$ alkyl, benzyl, phenethyl, adamantyl, or ($C_1$–$C_4$ carboalkoxy)methyl.

Specific preferred embodiments involve: ethyl N-[3,3-bis(p-chlorophenyl)acryloyl]glycinate, N-(1-adamantyl)-3,3-bis(p-chlorophenyl)propionamide, N-(1-adamantyl)-3,3-bis(p-methoxyphenyl)propionamide, N-(1-adamantyl)-3,3-bis(p-tolyl)propionamide, N,N-Dibenzyl-3,3-bis(p-methoxyphenyl)propionamide, N,N-Dibenzyl-3,3-bis(p-chlorophenyl)propionamide, N,N-Dibenzyl-3,3-bis(p-tolyl)propionamide, N,N-Di-(n-butyl)-3,3-bis(p-chlorophenyl)propionamide, N,N-Di-(n-butyl)-3,3-bis(p-methoxyphenyl)propionamide, N,N-Di-(n-butyl)-3,3-bis(p-tolyl)propionamide, N-Benzyl-3,3-bis(p-chlorophenyl)propionamide, or N-Butyl-3,3-bis(p-chlorophenyl)propionamide.

This invention also relates to a method of reducing the cholesterol content of the arterial walls of mammals which comprises administering to said mammal an effective amount of a compound as recited above.

This invention further relates to a method of inhibiting atherosclerotic lesion development in mammals which comprises administering to said mammal an effective amount of a compound as recited above.

This invention still further relates to a pharmaceutical composition which comprises an effective antiatherosclerotic amount of a compound as recited above in association with a pharmaceutically acceptable carrier.

Finally, this invention relates to a process for preparing compounds as recited above which comprises reacting an acid derivative of the formula:

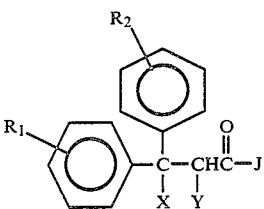

with an amine of the formula:

wherein $R_1$, $R_2$, $R_3$, $R_4$, X, and Y are as defined hereinabove, and J is selected from the group consisting of halo, $C_1$-$C_4$ alkoxy, and $C_1$-$C_4$ alkanoyloxy.

DETAILED DESCRIPTION OF THE INVENTION

Many of the compounds of this invention are prepared by reactions of diarylpropionyl and diarylacryloyl halides with primary and secondary amines. An example of this is the reaction of bis-$\beta,\beta$-(p-chlorophenyl)acryloyl chloride with ethyl glycinate. The reaction may be conducted in an organic solvent such as dichloromethane, chloroform, tetrahydrofuran, ether, 1,2-dimethoxyethane, acetone, hexane, and the like. Inorganic as well as organic bases such as triethylamine, 4-(dimethylamino)pyridine, and diisopropylethylamine may be used to catalyze the reaction, if necessary. Alternatively an excess of the amine undergoing reaction may be used. The reactions are run at temperatures at or below room temperature up to the boiling point of the solvent used.

The preparation of diarylpropionyl and diarylacrolyl halides required for the above-described acylation reactions may be accomplished by a variety of methods. Certain diarylacrolyl halides are prepared by the Wadsworth-Emmons reaction of triethylphosphonoacetate with a benzophenone followed by alkaline hydrolysis and acid chloride formation. An example of this sequence of reactions is the Wadsworth-Emmons reaction of triethylphosphonoacetate with 4,4'-dichlorobenzophenone which yields ethyl 3,3-bis-(p-chlorophenyl)acrylate. Alkaline hydrolysis of this acrylate ester affords 3,3-bis-(p-chlorophenyl)acryloyl chloride by reaction with thionyl chloride. Alternatively, the intermediate acrylate ester or acrylic acid may be catalytically hydrogenated to yield the corresponding propionate ester or propionic acid, respectively. Transformation of the propionate ester or the propionic acid to the corresponding diarylpropionyl halide is accomplished in the manner described for transformation of acrylate esters and acrylic acids to acryloyl halides.

Another method useful for the synthesis of the diarylpropionic and diarylacrylic acids required as intermediates, involves the alkylation of a benzophenone with the dianion derived from acetic acid followed by dehydration of the resulting hydroxy acid and, if required, catalytic hydrogenation. For instance, alkylation of 4,4'-dimethylbenzophenone with the dianion of acetic acid yields 3-hydroxy-3,3-bis-(p-tolyl)propionic acid. Acid-catalyzed dehydration of this acid affords 3,3-bis-(p-tolyl)acrylic acid. Finally, catalytic hydrogenation may be used to convert this acid to 3,3-bis-(p-tolyl)propionic acid.

Alternatively, 3,3-bis(p-tolyl)propionic acid may be obtained by a sequence of reactions involving: reduction of 4,4'-dimethylbenzophenone with lithium aluminum hydride; treatment of the resulting bis(p-tolyl)methanol with hydrogen chloride; alkylation of the diethyl malonate with the resulting bis(p-tolyl)methyl chloride; alkaline hydrolysis of the resulting diethyl[bis(p-tolyl)methyl]malonate using sodium hydroxide; and finally, decarboxylation of the resulting [bis(p-tolyl)methyl]malonic acid to yield 3,3-bis(p-tolyl)propionic acid.

A method useful for the preparation of diarylpropionic acids is Friedel-Crafts alkylation of activated aromatic compounds. An example of this is the reaction of anisole with 4-methoxycinnamic acid to yield bis-3,3-(p-methoxyphenyl)propionic acid.

The compounds of the present invention are generally obtained as crystalline solids having characteristic melting points and spectra. They are appreciably soluble in many organic solvents but are generally less soluble in water. Those compounds which are carboxylic acids may be converted to their alkali metal and alkaline earth salts by treatment with appropriate metal hydroxides, and these salts exhibit increased water solubility.

The preparation and properties of the compounds of this invention will be described in greater detail in conjunction with the specific examples shown below.

The compounds of the present invention were tested for their ability to inhibit the enzymatic esterification of cholesterol according to the following procedure:

Rat adrenals were homogenized in 0.2M monobasic potassium phosphate buffer, pH 7.4, and centrifuged at 1,000 times gravity for 15 minutes at 5° C. The supernatant, containing the microsomal fraction, served as the source of the cholesterol-esterifying enzyme, fatty acyl CoA:cholesterol acyl transferase (ACAT). A mixture comprising 50 parts of adrenal supernatant, 10 parts of albumin (BSA) (50 mg./ml.), 20 parts of oleoyl CoA ($^{14}$C-0.4 $\mu$Ci), 3 parts of test compound, and 500 parts of buffer was pre-incubated at 37° C. for 10 minutes. After treatment with 20 parts of oleoyl CoA ($^{14}$C-0.4 $\mu$Ci), the mixture was incubated at 37° C. for 10 minutes. A control mixture, omitting the test compound, was prepared and treated in the same manner. The lipids from the incubation mixture were extracted into an organic solvent and separated by thin-layer chromatography. The cholesterol ester fraction was counted in a scintillation counter. This procedure is a modification of that described by Hashimoto, et al., Life Scie., 12 (Part II), 1–12 (1973).

The results of this test on representative compounds of this invention appear in Table I. The final concentration of the test compound was 5.2 $\mu$g./ml., and effectiveness of the compound is expressed as percent inhibition of the ACAT enzyme compared to control values.

TABLE I

| COMPOUND | % INHIBITION |
| --- | --- |
| Ethyl N—[3,3-bis(p-chlorophenyl)acryloyl]glycinate | 85 |
| N—(1-Adamantyl)-3,3-bis(p-chlorophenyl)propionamide | 97 |
| N—(1-Adamantyl)-3,3-bis(p-methoxyphenyl)propionamide | 89 |
| N—(1-Adamantyl)-3,3-bis(p-tolyl)propionamide | 76 |
| N—[2-(3,4-Dimethoxyphenyl)ethyl]-3,3-bis(p- | 78 |

TABLE I-continued

| COMPOUND | % INHIBITION |
|---|---|
| methoxyphenyl)propionamide | |
| N,N—Dibenzyl-3,3-bis(p-methoxyphenyl)propiomide | 87 |
| N,N—Dibenzyl-3,3-bis(p-chlorophenyl)propiomide | 93 |
| N,N—Dibenzyl-3,3-bis(p-tolyl)propionamide | 68 |
| N—Benzyl-N—(n-butyl)-3,3-bis(p-chlorophenyl)propionamide | 45 |
| N,N—Di-(n-butyl)-3,3-bis(p-chlorophenyl)propionamide | 48 |
| N,N—Di-(n-butyl)-3,3-bis(p-methoxyphenyl)propionamide | 95 |
| N,N—Di-(n-butyl)-3,3-bis(p-tolyl)propionamide | 94 |
| N—Benzyl-3,3-bis(p-chlorophenyl)propionamide | 35 |
| N—(n-Butyl)-3,3-bis(p-chlorophenyl)propionamide | 92 |
| N,N—Dimethyl-3,3-bis(p-chlorophenyl)propionamide | 68 |
| 3,3-Bis(p-chlorophenyl)propionamide | 31 |

When the compounds are employed for the above utility, they may be combined with one or more pharmaceutically-acceptable carriers, e.g., solvents, diluents, and the like and may be administered orally in such forms as tablets, capsules, dispersible powders, granules, suspensions containing, for example, from about 0.5% to 5% of suspending agent, syrups containing, for example, from about 10% to 50% of sugar, and elixers containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed for the reduction of cholesterol ester content in the arterial walls of a mammal may vary depending on the particular compound employed, the mode of administration, and the severity of the condition being treated. In general, however, satisfactory results are obtained when the compounds of the invention are administered at a daily dosage of from about 2 milligrams to about 500 milligrams per kilogram of animal body weight, preferably given in divided doses two to four times a day, or in sustained release form. For most large mammals, the total daily dosage is from about 100 milligrams to about 5,000 milligrams preferably from about 100 milligrams to 2,000 milligrams. Dosage forms suitable for internal use comprise from about 25 to 2,500 milligrams of the active compound in intimate admixture with a solid or liquid pharmaceutically-acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes, if necessary. Solid carriers include starch, lactose, and kaoline, while liquid carriers include sterile water, polyethylene glycols, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT, and BHA.

The preferred pharmaceutical compositions from the stand-point of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically-acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

EXAMPLE 1

Ethyl N-[3,3-bis(p-chlorophenyl)acryloyl]glycinate

A 9.0 ml. portion of thionyl chloride is added to a solution of 9.0 g. of bis-$\beta,\beta$-(p-chlorophenyl)acrylic acid in 50 ml. of dichloromethane. The mixture is stirred under reflux for 4 hours, then evaporated, giving 9.98 g. of bis-$\beta,\beta$-(p-chlorophenyl)acryloyl chloride as an oil. This oil is dissolved in 50 ml. of dichloromethane and added portionwise to a stirred mixture of 4.19 g. of ethyl glycinate hydrochloride and 12.5 ml. of triethylamine in 50 ml. of dichloromethane. This mixture is stirred at reflux for 20 hours and then filtered. Evaporation of the filtrate gives a solid which is stirred with 250 ml. of boiling acetone and filtered while hot. The filtrate is concentrated by distillation to 150 ml. and then chilled. The second crop of solid formed is recrystallized from 40 ml. of acetonitrile, giving 2.87 g. of the desired product as a white solid, m.p. 123°–124° C.

EXAMPLE 2

N-[3,3-Bis(p-chlorophenyl)acryloyl]glycine

A mixture of 1.0 g. of ethyl N-[3,3-bis(p-chlorophenyl)acryloyl]glycinate, 106 mg. of sodium hydroxide, 18 ml. of ethanol, and 2 ml. of water is stirred under reflux for one hour, allowed to cool, diluted with 80 ml. of water, and acidified with 20 ml. of 1N hydrochloric acid. The solid is collected, dried in vacuo at 50° C., and then stirred with 50 ml. of dichloromethane and 50 ml. of water. The solid which fails to dissolve is collected and dried at 50° C., giving 150 mg. of the desired product as a white solid, m.p. 166°–168° C.

The diarylalkanamides, shown in Table II, were prepared from the appropriate diarylalkanoic acids and amines by the method of Example 1.

TABLE II

| EXAMPLE | COMPOUND | M.P., °C. |
|---|---|---|
| 3 | Ethyl N—[3,3-bis(p-tolyl)acryloyl]glycinate | |
| 4 | Ethyl N—[3,3-bis(p-methoxyphenyl)acryloyl]glycinate | |
| 5 | Ethyl N—[3,3-bis(phenyl)acryloyl]glycinate | |
| 6 | Ethyl N—[3,3-bis(p-chlorophenyl)propionyl]glycinate | |
| 7 | Ethyl N—[3,3-bis(p-tolyl)propionyl]glycinate | |
| 8 | Ethyl N—[3,3-bis(phenyl)propionyl]glycinate | |
| 9 | Ethyl N—[3,3-bis(p-methoxyphenyl)propionyl]glycinate | 84–86° |
| 10 | N—(1-Adamantyl)-3,3-bis(p-chlorophenyl)propionamide | 208–209° |
| 11 | N—(1-Adamantyl)-3,3-bis(p-methoxyphenyl)propionamide | 148–152° |
| 12 | N—(1-Adamantyl)-3,3-bis(phenyl)propionamide | |
| 13 | N—(1-Adamantyl)-3,3-bis(p-tolyl)propionamide | 192–196° |
| 14 | N—(1-Adamantyl)-3,3-bis(p-chlorophenyl)acrylamide | |
| 15 | N—(1-Adamantyl)-3,3-bis(p-methoxyphenyl)acrylamide | |
| 16 | N—[2-(3,4-Dimethoxyphenyl)ethyl]-3,3-bis(p-chlorophenyl)acrylamide | |
| 17 | N—[2-(3,4-Dimethoxyphenyl)ethyl]-3,3-bis(p-tolyl)acrylamide | |
| 18 | N—[2-(3,4-Dimethoxyphenyl)ethyl]-3,3-bis(p-methoxyphenyl)propionamide | 121–123° |
| 19 | N—[2-(3,4-Dimethoxyphenyl)ethyl]-3,3-bis(p-chlorophenyl)propionamide | |
| 20 | N—(2-Phenylethyl)-3,3-bis(p-chlorophenyl)acrylamide | |
| 21 | N—(2-Phenylethyl)-3,3-bis(p-tolyl)propionamide | |
| 22 | N—Benzyl-3,3-bis(p-chlorophenyl)acrylamide | |
| 23 | N—Benzyl-3,3-bis(p-tolylphenyl)acrylamide | |
| 24 | N—Benzyl-3,3-bis(phenyl)acrylamide | |
| 25 | N—Benzyl-3,3-bis(p-chlorophenyl)propionamide | 202–204° |
| 26 | N—Benzyl-3,3-bis(p-methoxyphenyl)propionamide | |
| 27 | N,N—Dibenzyl-3,3-bis(p-chlorophenyl)acrylamide | |
| 28 | N,N—Dibenzyl-3,3-bis(p-tolyl)acrylamide | |
| 29 | N,N—Dibenzyl-3,3-bis(p-methoxyphenyl)propionamide | 112–114° |
| 30 | N,N—Dibenzyl-3,3-bis(p-chlorophenyl)propionamide | 140–142° |
| 31 | N,N—Dibenzyl-3,3-bis(p-tolyl)propionamide | 79–82° |
| 32 | N—Benzyl-N—(n-butyl)-3,3-bis(p-tolyl)acrylamide | |
| 33 | N—Benzyl-N—(n-butyl)-3,3-bis(p-methoxyphenyl)acrylamide | |
| 34 | N—Benzyl-N—(n-butyl)-3,3-bis(p-methoxyphenyl)propionamide | Oil |
| 35 | N—Benzyl-N—(n-butyl)-3,3-bis(p-tolyl)propionamide | |
| 36 | N—Benzyl-N—(n-butyl)-3,3-bis(p-chlorophenyl)propionamide | 80–82° |
| 37 | N—benzyl-N—(n-butyl)-3,3-bis(phenyl)propionamide | |
| 38 | N,N—Di-(n-butyl)-3,3-bis(phenyl)acrylamide | |
| 39 | N,N—Di-(n-butyl)-3,3-bis(p-tolyl)acrylamide | |
| 40 | N,N—Di-(n-butyl)-3,3-bis(p-chlorophenyl)acrylamide | |
| 41 | N,N—Di-(n-butyl)-3,3-bis(p-chlorophenyl)propionamide | Oil |
| 42 | N,N—Di-(n-butyl)-3,3-bis(p-methoxyphenyl)propionamide | 36–40° |
| 43 | N,N—Di-(n-butyl)-3,3-bis(p-tolyl)propionamide | 57–58° |
| 44 | N,N—Di-(n-butyl)-3,3-bis(phenyl)propionamide | |
| 45 | N—(n-Butyl)-3,3-bis(p-chlorophenyl)acrylamide | |
| 46 | N—(n-Butyl)-3,3-bis(p-tolyl)acrylamide | |
| 47 | N—(n-Butyl)-3,3-bis(p-chlorophenyl)propionamide | 100–102° |
| 48 | N—(n-Butyl)-3,3-bis(p-methoxyphenyl)propionamide | |
| 49 | N,N—Dimethyl-3,3-bis(phenyl)propionamide | |
| 50 | N,N—Dimethyl-3,3-bis(p-chlorophenyl)propionamide | 144–147° |
| 51 | N,N—Dimethyl-3,3-bis(p-methoxyphenyl)propionamide | |
| 52 | N,N—Dimethyl-3,3-bis(p-chlorophenyl)acrylamide | |
| 53 | N,N—Di-(n-octyl)-3,3-bis(p-chlorophenyl)propionamide | |
| 54 | N,N—Di-(n-decyl)-3,3-bis(p-chlorophenyl)propionamide | |
| 55 | 3,3-Bis(p-chlorophenyl)acrylamide | |
| 56 | 3,3-Bis(p-methoxyphenyl)acrylamide | |
| 57 | 3,3-Bis(p-tolyl)acrylamide | |
| 58 | 3,3-Bis(p-chlorophenyl)propionamide | 159–161° |
| 59 | 3,3-Bis(p-tolyl)propionamide | |
| 60 | 3,3-Bis(phenyl)propionamide | |
| 61 | 3,3-Bis(p-methoxyphenyl)propionamide | 168–170° |

The diarylalkanamides shown in Table III were prepared from the appropriate diarylalkanamido esters by the method of Example 2.

TABLE III

| EXAMPLE | COMPOUND | M.P., °C. |
|---|---|---|
| 62 | N—[3,3-Bis(p-methoxyphenyl)acryloyl]glycine | |
| 63 | N—[3,3-Bis(p-tolyl)acryloyl]glycine | |
| 64 | N—[3,3-Bis(phenyl)acryloxyl]glycine | |
| 65 | N—[3,3-Bis(p-chlorophenyl)propionyl]glycine | |
| 66 | N—[3,3-Bis(p-methoxyphenyl)propionyl]glycine | White Solid |
| 67 | N—[3,3-Bis(p-tolyl)propionyl]glycine | |
| 68 | N—[3,3-Bis(phenyl)propionyl]glycine | |

EXAMPLE 69

Ethyl 3,3-bis(p-chlorophenyl)acrylate

A suspension of 19.1 g. (0.398 mole) of sodium hydride (50% in mineral oil) in 1.2 l. of 1,2-dimethoxyethane is stirred under argon while 89.3 g. (0.398 mole) of triethylphosphonoacetate was added dropwise. The mixture is stirred at approximately 25° for 30 minutes and then treated portion-wise with 100 g. (0.398 mole) of 4,4′-dichlorobenzophenone during 30 minutes. The supernatant liquid is decanted, extracted with water and evaporated to yield ethyl 3,3-bis(p-chlorophenyl)acrylate as a white solid. Purification by recrystallization from ethanol yields 2.3 g. of the ester as a white solid, m.p. 54°–56° C.

EXAMPLE 70

3,3-Bis(p-chlorophenyl)acrylic acid

A solution of 3.21 g. (10.0 mmol) of ethyl 3,3-bis(p-chlorophenyl)acrylate and 1.15 g. of 85% potassium hydroxide in 50 ml. of 95% ethanol is stirred at approximately 75° C. for 4 hours, diluted with water, and acidified with hydrochloric acid. The precipitate is collected and recrystallized from toluene to yield 3.37 g. of 3,3-bis(p-chlorophenyl)acrylic acid, m.p. 177°–179° C.

Prepared in a similar manner in 95% yield from ethyl 3,3-bis(p-chlorophenyl)propionate was 3,3-bis(p-chlorophenyl)propionic acid, m.p. 190°–193° C.

EXAMPLE 71

3,3-Bis(p-chlorophenyl)acryloyl chloride

A stirred solution of 433 g. (1.48 moles) of 3,3-bis(p-chlorophenyl)acrylic acid in 3.2 l. of toluene is treated with 500 g. of thionyl chloride and then heated at approximately 80° for 5 hours. The solution is allowed to cool and evaporated in vacuo to yield 491 g. of 3,3-bis(p-chlorophenyl)acryloyl chloride as a tan solid.

EXAMPLE 72

Ethyl 3,3-bis(p-chlorophenyl)propionate

A mixture of 32.1 g. (0.100 mole) of ethyl 3,3-bis(p-chlorophenyl)acrylate, 1.60 g. of platinum oxide, and 250 ml. of cyclohexane is shaken under 40 lbs. of hydrogen in a Parr apparatus approximately 6 hours and then filtered and evaporated. The resulting solid is crystallized from ethanol to yield 22.8 g. of ethyl 3,3-bis(p-chlorophenyl)propionate as a white solid, m.p. 48°–52° C.

Prepared in a similar manner from 3,3-bis(p-chlorophenyl)acrylic acid was 3,3-bis(p-chlorophenyl)propionic acid, m.p. 190°–193° C.

EXAMPLE 73

3,3-Bis(p-methoxyphenyl)propionic acid

A mixture of 10.0 g. (56 mmol) of p-methoxycinnamic acid is warmed at approximately 75° C. and treated with 6.07 g. (56 mmol) of anisole and heated at 75° C. for about 18 hours. The mixture is cooled and poured into water. The solid is collected by filtration and recrystallized from methylene chloride hexane to yield 16.2 g. of 3,3-bis(p-methoxyphenyl)propionic acid, m.p. 132°–134° C.

EXAMPLE 74

3,3-Bis(p-tolyl)propionic acid

A suspension of 1.6 g. (942 mmol) of lithium aluminum hydride and 250 ml. of ether is stirred under reflux while 30 g. (143 mmol) of 4,4'-dimethylbenzophenone was added and for 4 hours thereafter. The mixture is cautiously treated with water and dilute sodium hydroxide and filtered. Evaporation of the filtrate yields 28.1 g. of bis(p-tolyl)methanol, m.p. 69°–70° C.

A solution of 28.1 g. (13 mmol) of bis(p-tolyl)methanol in 200 ml. of ether was treated with anhydrous hydrogen chloride and then filtered. Evaporation of the filtrate followed by recrystallization from petroleum ether yields 24.4 g. of bis(p-tolyl)methyl chloride, m.p. 42°–43° C.

A suspension of 11.5 g. (0.24 mole) of sodium hydride (50% in mineral oil) in 250 ml. of anhydrous tetrahydrofuran is stirred under argon while a solution of 38.4 g. (0.24 mole) of diethyl malonate in 100 ml. of tetrahydrofuran is added. The mixture is then treated with 16 g. (0.11 mole) of sodium iodide followed by a solution of 25 g. (0.11 mole) of bis(p-tolyl)methyl chloride in 100 ml. of tetrahydrofuran. The resulting mixture is stirred for 4 days at approximately 25° C. and then poured into ice and extracted with ether. The extract is dried and evaporated and the residue crystallized from petroleum ether to yield 26.1 g. of diethyl [bis(p-tolyl)methyl]malonate, m.p. 74°–75° C.

A mixture of 29.5 g. (83 mmol) of diethyl [bis(p-tolyl)methyl]malonate, 100 ml. of ethanol, and 100 ml. of 5N sodim hydroxide is stirred under reflux for 3 hours and then evaporated. The residue is dissolved in water, and the solution filtered and then acidified. The precipitate is collected by filtration and dried to yield 23.5 g. of [bis(p-tolyl)methyl]malonic acid, m.p. 188°–191° C.

A 23 g. (77 mmol) quantity of [bis(p-tolyl)methyl]malonic acid is heated at approximately 190° C. for 5 minutes, allowed to cool, and crystallized from ethanol to yield 15.1 g. of 3,3-bis(p-tolyl)propionic acid, m.p. 183°–184° C.

No effort has been made to optimize the yields obtained in the aforementioned Examples.

We claim:

1. The compound, ethyl N-[3,3-bis(p-chlorophenyl)acryloyl]glycinate.
2. The compound, N-(1-adamantyl)-3,3-bis-(p-chlorophenyl)propionamide.
3. The compound, N-(1-adamantyl)-3,3-bis(p-methoxyphenyl)propionamide.
4. The compound, N-(1-adamantyl)-3,3-bis(p-tolyl)propionamide.
5. A method of reducing the cholesterol ester content of the arterial walls of a mammal in need of such treatment which comprises administering to said mammal an effective amount of a compound of the formula:

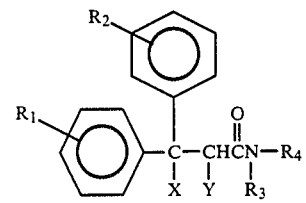

wherein $R_1$ and $R_2$ are the same or different and are independently selected from the group consisting of hydrogen, $C_1$–$C_4$ alkyl, $C_1$–$C_4$ alkoxy, and halo; X and Y are each hydrogen, or, when taken together, represent a carbon-carbon bond; $R_3$ and $R_4$ are the same or different and are independently selected from the group consisting of hydrogen, $C_1$–$C_{10}$ alkyl, benzyl, phenethyl, 3,4-dimethoxyphenethyl, adamantyl, carboxymethyl, and ($C_1$–$C_4$ carboalkoxy)methyl with the proviso that $R_3$ and $R_4$ cannot both be hydrogen; and the pharmaceutically-acceptable salts thereof.

6. A method of treating atherosclerosis in a mammal in need of such treatment which comprises administering to said mammal in antiatherosclerotic amount of a compound of the formula:

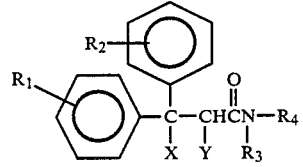

wherein $R_1$ and $R_2$ are the same or different and are independently selected from the group consisting of hydrogen, $C_1$–$C_4$ alkyl, $C_1$–$C_4$ alkoxy, and halo; X and Y are each hydrogen or, when taken together, represent a carbon-carbon bond; $R_3$ and $R_4$ are the same or different and are independently selected from the group consisting of hydrogen, $C_1$–$C_{10}$ alkyl, benzyl, phenethyl, 3,4-dimethoxyphenethyl, adamantyl, carboxymethyl, and ($C_1$–$C_4$ carboalkoxy)methyl with the proviso that $R_3$ and $R_4$ cannot both be hydrogen; and the pharmaceutically-acceptable salts thereof.

7. A method of inhibiting atherosclerotic lesion development in a mammal in need of such treatment which comprises administering to said mammal an effective amount of a compound of the formula:

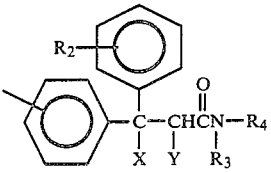

wherein $R_1$ and $R_2$ are the same or different and are independently selected from the group consisting of hydrogen, $C_1$–$C_4$ alkyl, $C_1$–$C_4$ alkoxy, and halo; X and Y are each hydrogen or, when taken together, represent a carbon-carbon bond; $R_3$ and $R_4$ are the same or different and are independently selected from the group consisting of hydrogen, $C_1$–$C_{10}$ alkyl, benzyl, phenethyl, 3,4-dimethoxyphenethyl, adamantyl, carboxymethyl, and ($C_1$–$C_4$ carboalkoxy)methyl with the proviso that $R_3$ and $R_4$ cannot both be hydrogen; and the pharmaceutically-acceptable salts thereof.

* * * * *